United States Patent
Utterodt et al.

(10) Patent No.: US 11,219,505 B2
(45) Date of Patent: Jan. 11, 2022

(54) DENTAL COMPOSITE MATERIAL AND MILL BLANKS CONSISTING OF SAID COMPOSITE MATERIAL

(71) Applicant: KULZER GMBH, Hanau (DE)

(72) Inventors: Andreas Utterodt, Neu-Anspach (DE); Kurt Reischl, Merenberg (DE); Nelli Schönhof, Braunfels (DE); Michael Eck, Schmitten (DE); Raif Kocoglu, Grävenwiesbach (DE); Jutta Schneider, Runkel (DE); Caroline Kempka, Wölfersheim (DE)

(73) Assignee: Kulzer GmbH, Hanau (DE)

( * ) Notice: Subject to any disclaimer, the term of this patent is extended or adjusted under 35 U.S.C. 154(b) by 0 days.

(21) Appl. No.: 16/753,428

(22) PCT Filed: Oct. 1, 2018

(86) PCT No.: PCT/EP2018/076600
§ 371 (c)(1),
(2) Date: Apr. 3, 2020

(87) PCT Pub. No.: WO2019/068618
PCT Pub. Date: Apr. 11, 2019

(65) Prior Publication Data
US 2020/0253691 A1 Aug. 13, 2020

(51) Int. Cl.
| | | |
|---|---|---|
| *A61C 5/73* | (2017.01) | |
| *A61C 5/20* | (2017.01) | |
| *A61C 5/77* | (2017.01) | |
| *A61K 6/77* | (2020.01) | |
| *A61K 6/30* | (2020.01) | |
| *A61K 6/17* | (2020.01) | |
| *A61C 8/00* | (2006.01) | |
| *A61C 13/00* | (2006.01) | |
| *A61C 13/271* | (2006.01) | |

(52) U.S. Cl.
CPC .................. *A61C 5/73* (2017.02); *A61C 5/20* (2017.02); *A61C 5/77* (2017.02); *A61C 8/0016* (2013.01); *A61C 13/0022* (2013.01); *A61C 13/26* (2013.01); *A61K 6/17* (2020.01); *A61K 6/30* (2020.01); *A61K 6/77* (2020.01); *A61C 2201/00* (2013.01)

(58) Field of Classification Search
CPC ....................................................... A61K 6/887
See application file for complete search history.

(56) References Cited

U.S. PATENT DOCUMENTS

| | | | |
|---|---|---|---|
| 4,323,696 A * | 4/1982 | Schmitz-Josten | ...... A61K 6/887 560/220 |
| 4,952,614 A | 8/1990 | Reiners et al. | |
| 8,556,198 B2 | 10/2013 | Schoen et al. | |
| 9,023,916 B2 | 5/2015 | Blomker et al. | |
| 9,326,918 B2 | 5/2016 | Utterodt et al. | |
| 2009/0036565 A1 | 2/2009 | Utterodt et al. | |
| 2010/0076115 A1 | 3/2010 | Utterodt et al. | |
| 2010/0087565 A1 | 4/2010 | Utterodt et al. | |
| 2012/0082958 A1 * | 4/2012 | Blomker | ................... A61K 6/17 433/219 |
| 2012/0295111 A1 | 11/2012 | Schoen et al. | |
| 2013/0261218 A1 | 10/2013 | Utterodt et al. | |

FOREIGN PATENT DOCUMENTS

| | | |
|---|---|---|
| DE | 10 2012 203 875 A1 | 10/2012 |
| EP | 0 254 185 A1 | 1/1988 |
| EP | 2 016 931 A2 | 1/2009 |
| EP | 2 436 365 A2 | 4/2012 |
| EP | 2 644 183 A2 | 10/2013 |

* cited by examiner

Primary Examiner — Michael F Pepitone
(74) Attorney, Agent, or Firm — Norris McLaughlin, P.A.

(57) ABSTRACT

A polymerisable dental composite material comprising
(i) 70 to 85% by weight of an inorganic filler component comprising at least one dental glass and optionally at least one amorphous metal oxide,
(ii) 10 to 30% by weight of a mixture of at least two different urethane(meth)acrylates,
(iii) 0.01 to 5% by weight of at least one di-, tri-, tetra- or multi-functional monomer not being a urethane(meth) acrylate,
(iv) 0.01 to 10% by weight of at least one initiator, of an initiator system and optionally of at least one stabilizer and optionally of at least one pigment, wherein the total composition of the composite material amounts to 100% by weight, as well as a polymerized composite material having a flexural strength of greater than or equal to 200 MPa and an elastic modulus of 15 to 20 GPa for the production of indirect dentures.

18 Claims, No Drawings

DENTAL COMPOSITE MATERIAL AND MILL BLANKS CONSISTING OF SAID COMPOSITE MATERIAL

This application is a 371 of PCT/EP2018/076600, filed Oct. 1, 2018, which claims foreign priority benefit under 35 U.S.C. § 119 of the German Patent Application No. 10 2017 123 009.2, filed Oct. 4, 2017, the disclosures of which are incorporated herein by reference.

The invention relates to a polymerisable dental composite material, comprising (i) 70 to 85% by weight of at least one inorganic filler component comprising at least one dental glass of an average particle size $d_{50}$ of 0.7 to 7.5 µm as well as optionally at least one amorphous metal oxide, (ii) 10 to 30% by weight of a mixture of at least two different urethane(meth)acrylates, (iii) 0.01 to 5% by weight of at least one di-, tri-, tetra- or multi-functional monomer not being a urethane(meth)acrylate, and (iv) 0.01 to 10% by weight of at least one initiator, of an initiator system as well as optionally stabilizers and optionally pigments, wherein the total composition of the composite material amounts to 100% by weight, as well as a polymerized composite material having a flexural strength of greater than or equal to 200 MPa and an elastic modulus of 15 to 20 GPa (dry storage).

Many dental composites universally usable for a direct adhesive restoration as well as for the extraoral fabrication of indirect dentures are known. From the material class of dental composites, only inorganic-organic hybrid materials with larger amounts of inorganic filling materials such as e.g. dental glass and/or mineral nano agglomerates are suitable. Micro filler composites with pre-polymer fillers introduced in the 1980s are not suitable for use in the posterior region (classes I and II) due to the limited wear resistance (abrasion resistance).

A high filler content is advantageous in order to achieve very good mechanical properties of the cured composite and to reduce the polymerization shrinkage that occurs during curing at the same time. These properties are also decisive for the long-term success of the denture material.

The excellent material properties of dental composites with polyalicyclic structural elements for direct adhesive restoration, especially the low shrinkage force and high flexural strength, are well known.

It was the object of the invention to provide a dental composite material being suitable for the production of larger blocks of material, in particular of geometric moulded bodies such as milling blocks. In addition, the object was to provide a dental composite material having a homogeneous, monochrome coloring before and after polymerization. In this context, the homogeneous, monochrome coloring should also be feasible with larger blocks of material. Furthermore, polychrome, i.e. multi-colored blocks of material with a defined coloring should be producible. Moreover, a dental composite material should be provided that is easily flowable in the non-polymerized state and yet has excellent mechanical properties in the polymerized state and has low shrinkage during polymerization, even when producing larger blocks of material. Furthermore, the composite material should not develop cracks or pores during curing, even with large-volume blocks of material.

Starting from state-of-the-art composites based on urethane derivatives, the filler system, the monomer mixture as well as the pigment system had to be modified. The wide particle size distribution, advantageous for high packing density and excellent mechanical properties, could not be maintained. According to the invention, a narrow particle size distribution was developed. The average value of the particle size distribution was set to a range of 0.7 µm to 7.5 µm. In this context, two alternatives are set being based on a content of 5 to 75% by weight of a dental glass having a particle size distribution of $d_{50}$ of a dental glass fraction in the range of 1.2 to 1.7 µm (micrometers), based on the total composition, preferably with $d_{50}$ of 1.5 µm with plus/minus 0.25 µm, particularly preferably $d_{99}$ less than or equal to 5 µm or $d_{99}$ less than or equal to 10 µm. Further dental glass fractions having differently smaller and/or larger particle size distribution may be added to these two alternatives to adjust the packing density optimally. The adjusted packing density enables optimal setting of the mechanical properties and of a reduced shrinkage.

Voluminous moulded parts for the production of larger blocks of material cannot be photo-polymerized due to the limited penetration depth of the light into the composite material. For this reason, the initiator system had to be adapted and further developed by using at least one thermally initiatable peroxide. In addition, it was necessary to avoid discolorations of existing photoinitiators due to thermal reactions or the significantly increased material dimension in the blocks of material. Therefore, usual blue light photoinitiators, such as the camphorquinone initiator system, were excluded in order to avoid color changes due to the composite layer thickness. When choosing the initiator system, care must be taken that, on the one hand, no stresses are built up in the large blocks of material due to the reaction kinetics, for example of a peroxide, in order to avoid cracking in the interior of the blocks, since the thermal conductivity of the materials is low.

Moulding for the production of the blocks of material is carried out by inserting the polymerizable dental composite material into a casting mould, hereinafter only referred to as mould, in particular under pressure. The applied pressure is preferably between 500 and 300 MPa or [N/mm2]. Polymerization is performed at elevated temperature, preferably being in the range of about 90 to 150° C. The polymerization is carried out at a pressure of about 90 to 300 MPa or [N/mm2]. It is polymerized in a closed casting mould to minimise, preferably avoid, the formation of air bubbles. Preferably, it is polymerized under a pressure of 120 to 320 MPa, preferably to less than or equal to 300 MPa and/or at a temperature of 100 to 180° C., preferably about 140° C., for at least 10 minutes to 10 hours. The blocks of material preferably have a dimension of at least 1 cm in all special directions and are present as geometric moulded bodies.

Surprisingly, it has been found that composites based on a urethane monomer having an alicyclic structural element, such as tetrahydrodicyclopentadiene, are extremely well suited for the production of indirect dentures, since surprisingly high flexural strengths may be achieved by thermally initiated polymerization. The high level of polymer strength compared to the already described photopolymerization in the case of light-curing dental composites was surprising and not to be expected with these significantly increased values. At the same time, the low-shrinkage crosslinking of the relatively large amount of composite in one process step is advantageous in order to avoid stress cracks in the block/blank. High crosslinking densities being desirable for material strength can often result in unusability of the polymerized molded parts due to the high shrinkage stresses.

A subject matter of the invention is a polymerisable dental composite material, in particular a thermally polymerisable composite material, comprising
(i) 70 to 85% by weight of at least one inorganic filler component comprising at least one dental glass of an average particle size $d_{50}$ of 0.7 to 7.5 µm, in particular of 0.7 to 5.5 µm, preferably of 0.8 to 5.5 µm, as well as optionally at least one amorphous metal oxide,
(ii) 10 to 30% by weight of a mixture of at least two different urethane(meth)acrylates, preferably of a mixture of at least three different urethane(meth)acrylates, in particular of di- to decafunctional urethane(meth)acrylates,
(iii) 0.01 to 5% by weight of at least one di-, tri-, tetra- or multi-functional monomer not being a urethane(meth)acrylate,
(iv) 0.01 to 10% by weight of at least one initiator, of an initiator system as well as optionally of at least one stabilizer and optionally of at least one pigment, wherein in particular the at least one pigment comprises both fluorescence pigments and color pigments, wherein the total composition of the composite material amounts to 100% by weight.

In one embodiment variant, it is preferred for the thermally polymerisable composite material to be additionally photochemically polymerisable. A thermally polymerisable composite material is presently understood to mean a composite material that may be polymerized at greater than or equal to 60 to 150° C., preferably at greater than or equal to 70 to 150° C., particularly preferably from 90 to 150° C. In this context, according to the invention it is further preferred for the volume shrinkage to be less than or equal to 1.5%.

By polymerizing the composite material according to the invention, a polymerized composite material having a flexural strength of greater than or equal to 200 MPa, in particular greater than or equal to 220 MPa, and an elastic modulus of 15 to 20 GPa, in particular 16 GPa to 20 GPa at dry storage is obtainable. Said composite material preferably has a flexural strength of greater than or equal to 170 MPa and an elastic modulus of 14 to 21 GPa after storage in deionized water for 7 days at 37° C. followed by thermocycling. The polymerized composite material is preferably present as block of material, in particular in the form of a milling blank having a dimension of at least 10 mm in all spatial directions.

The composite material according to the invention is thermally polymerisable, wherein a polymerized composite material having a flexural strength of greater than or equal to 200 MPa to 260 MPa (7 days, 23±2° C., dry) and an elastic modulus greater than or equal to 15 to 20 GPa (7 days, 23±2° C., dry) according to EN ISO 6872:2008 is obtainable, in particular having a flexural strength of greater than or equal to 210 MPa, preferably greater than or equal to 220 MPa and an e-modulus of greater than or equal to 16 to 20 GPa, preferably of greater than or equal to 17 GPa to 20 GPa, further preferably of 18 to 20 GPa. Furthermore, a subject matter of the invention is thermally polymerisable composite material, wherein a polymerized composite material having a flexural strength of greater than or equal to 160 MPa to 260 MPa (7 days stored in $H_2O$ deionized at 37° C., followed by greater than or equal to 1000 cycles, in particular by greater than or equal to ca. 5000 cycles (5° C. to 55° C., retention time greater than or equal to 30 seconds, optionally to 60 seconds)) and an elastic modulus greater than or equal to 14 to 21 GPa (7 days stored in $H_2O$ deionized at 37° C., followed by greater than or equal to 1000 cycles, in particular by. 5000 cycles (5° C. to 55° C., retention time greater than or equal to 30 seconds)) according to EN ISO 6872:2008 is obtainable, in particular having a flexural strength of greater than or equal to 170 MPa, preferably greater than or equal to 210 MPa and an e-modulus of greater than or equal to 15 to 21 GPa, preferably of greater than or equal to 16 GPa to 20 GPa, further preferably of 18 to 21 GPa. Preferably, the thermally polymerized composite material has the two afore-mentioned properties (dry and after thermocycling).

In one embodiment variant, it is particularly preferred for the inorganic filler component to consist of at least a dental glass or a mixture of dental glasses, in particular of an aforementioned average particle size and an amorphous metal oxide, in particular a non-agglomerated amorphous metal oxide, preferably a silanised amorphous metal oxide. The dental glass may preferably also be silanised.

The following dental glasses are preferably considered: aluminosilicate glasses or fluoroaluminosilicate glasses, barium aluminum silicate, strontium silicate, strontium borosilicate, lithium silicate and/or lithium aluminum silicate as well as mixtures of at least two of the aforementioned dental glasses. Amorphous spherical fillers based on oxide or mixed oxide, such as amorphous $SiO_2$, $ZrO_2$ or mixed oxides of $SiO_2$ and $ZrO_2$, may be used as metal oxide or as a mixture of amorphous metal oxides.

A subject matter of the invention is also a dental composite material comprising
a) a dental glass of an average particle size $d_{50}$ of 1.5 µm with plus/minus 0.25 µm and preferably $d_{99}$ less than or equal to 10 µm, or
b) a dental glass comprising a mixture of dental glasses of different fractions having average particle sizes with i) $d_{50}$ of 2 to 8 µm optionally with plus/minus 0.5 µm, in particular with 4 to 6 µm optionally with plus/minus 0.25 µm, ii) $d_{50}$ of 1.0 to 2.0 µm optionally with plus/minus 0.25 µm, in particular with 1.2 to 1.7 pm optionally with plus/minus 0.5 µm, preferably with 1.5 pm optionally with plus/minus 0.15 µm, and iii) $d_{50}$ of 0.5 µm to 1.2 µm optionally with plus/minus 0.15 µm, 0.7 to 0.9 µm optionally with plus/minus 0.5 µm, wherein the fractions of i) to ii) to iii) are present in the ratio of 1 to 4:1:4 to 8, in particular of 2 to 3:1:6 to 7. Particularly preferred is i) $d_{50}$ of 5 µm optionally with plus/minus 0.5 µm, ii) $d_{50}$ of 1.5 µm optionally with plus/minus 0.25 µm and iii) $d_{50}$ of 0.85 µm optionally with plus/minus 0.15 µm, wherein the fraction of i) to ii) to iii) are present in the ratio of 1 to 4:1:4 to 8, in particular of 2 to 3:1:6 to 7.

According to a preferred embodiment, the dental composite material comprises at least one dental glass, in particular a radiopaque dental glass, of an average particle size $d_{50}$ of 1.2 to 1.7 µm, preferably having an average particle size of 1.35 to 1.65 µm, in particular with $d_{50}$ of 1.5 µm optionally plus/minus 0.15 µm, and preferably with $d_{99}$ less than or equal to 10 µm, Particularly preferably, a dental glass is additionally present having an average particle size of $d_{50}$ of about 0.85 µm optionally plus/minus 0.1 µm, in particular plus/minus 0.05 µm, preferably plus/minus 0.03 µm, and preferably with $d_{99}$ less than or equal to 10 µm. A particularly preferred dental glass comprises barium aluminum borosilicate glass. Moreover, a barium aluminum silicate glass having a reflective index of n=1.52 to 1.55, preferably 1.53, is particularly preferred. A particularly preferred particle size distribution may be in the range of $d_{10}$ with greater than or equal to 0.2 µm to $d_{99}$ less than or equal to 7.5 µm, preferably with $d_{10}$ greater than or equal to 0.4 µm to $d_{99}$ less than or equal to 7.5 µm and an average diameter $d_{50}$ of 0.7 to 7.5 µm.

According to a preferred embodiment, the dental composite material comprises
(i) 70 to 85% by weight of at least one inorganic filler component, wherein at least one dental glass of an average particle size $d_{50}$ of 0.7 to 2.0 µm is present of greater than or equal to 50 to 80% by weight, based on the composite material, in particular of greater than or equal to 55 to 76% by weight, preferably greater than or equal to 60 to 75% by weight, particularly preferably greater than or equal to 60 to 71% by weight in the total composition. Further preferably in combination with an amorphous silicon dioxide with 4 to 7.5% by weight in the total composition.

Furthermore, a subject matter of the invention is a dental composite material comprising (i) 70 to 85% by weight of at least one inorganic filler component comprising at least one dental glass comprising barium aluminum borosilicate glass, barium aluminum borfluorosilicate glass, in particular silanised, preferably functionalised with methacryloxypropyl groups, as well as optionally at least one non-agglomerated amorphous metal oxide of a primary particle size of 2 to 45 nm, wherein the amorphous metal oxide comprises precipitated silicon dioxide, zirconium oxide, mixed oxides or mixtures thereof, in particular the metal oxides are silanised.

In order to achieve a high flexural strength, the dental composite material preferably comprises as inorganic filler component (i.1) 66 to 84% by weight of at least one dental glass, in particular from 68 to 78% by weight, alternatively from 75 to 78% by weight, and optionally (i.2) 2 to 10% by weight amorphous metal oxide, in particular from 3 to 10% by weight, preferably 4 to 8% by weight, in the total composition. The ratio of dental glass to amorphous metal oxide preferably amounts to 20:1 to 5:1, preferably to 15:1 to 10:1

Preferably, from 85 to 99% by weight of at least one dental glass or a mixture of dental glasses, preferably from 91 to 99% by weight, alternatively 92 to 99% by weight, and optionally 1 to 13% by weight, in particular 8 to 15% by weight, alternatively 1 to 8% by weight amorphous metal oxide or mixture of metal oxides, in particular pyrogenic silica and/or precipitated silicon dioxide, are present in the inorganic filler component.

According to a particularly preferred embodiment, the dental composite material comprises
(i) 70 to 85% by weight of at least one inorganic filler component comprising (i.1) 60 to 84% by weight, in particular from 66 to 78% by weight, preferably 66 to 70% by weight or 75 to 78% by weight at least one dental glass of an average particle size $d_{50}$ of 0.7 to 7.5 μm, in particular from 1.5 μm optionally with an afore-mentioned standard deviation, as well as optionally (i.2) 1 to 34% by weight, in particular from 3 to 15% by weight, preferably 3 to 10% by weight, particularly preferably 4 to 10% by weight of at least one amorphous silanised metal oxide and/or pyrogenic silica of a primary particle size of 2 to 45 nm, based on the total composition,
(ii) 10 to 30% by weight, in particular from 15 to 30% by weight, preferably 18 to 22% by weight of a mixture of at least two different urethane(meth)acrylates, in particular of di- to decafunctional urethane(meth)acrylates, preferably from 15 to 19% by weight of a difunctional urethane (meth)acrylate having a bivalent alicyclic group and 5 to 6% by weight of a difunctional urethane(meth)acrylate having a bivalent alkylene group, and optionally 0.1 to 2% by weight of at least one hexafunctional urethane (meth)acrylate or dendritic urethane methacrylate of a mixture of urethane(meth)acrylates, and
(iii) 0.01 to 5% by weight, in particular 0.5 to 3% by weight, preferably 0.8 to 2.0% by weight, of at least one di-, tri-, tetra- or multi-functional monomer not being a urethane (meth)acrylate, in particular at least one di-, tri-, tetra- or multi-functional methacrylic ester of polyethers, preferably dimethacrylate triethylene glycol,
(iv) 0.01 to 10% by weight, in particular 0.5 to 5% by weight, preferably 0.5 to 2% by weight of at least one thermal initiator, of a thermal initiator system as well as optionally of at least one stabilizer and optionally of at least one pigment, in particular of a pigment mixture comprising a pigment selected from fluorescence pigments and color pigments, wherein the total composition of the composite material amounts to 100% by weight.

The di- to decafunctional urethane(meth)acrylates are used as monomers and do not comprise peroxy groups.

According to a particularly preferred embodiment, the dental composite material comprises
(ii) 10 to 30% by weight of a mixture of at least two different urethane(meth)acrylates, preferably of three different urethane(meth)acrylates, comprising at least one difunctional urethane(meth)acrylate having a bivalent alicyclic group in particular comprising bis(4',7'-dioxa-3',8'-dioxo-2'-aza-decyl-9'-en)tetrahydrodicyclopentadiene, bis(4',7'-dioxa-3',8'-dioxo-2'-aza-9'-methyl-decyl-9'-en)tetrahydrodicyclopentadiene and/or mixtures thereof, as well as optionally mixtures of the 3,8-/3,9-/4,8-/3,10-/4,10 isomers and/or of the cis isomers and trans isomers of the afore-mentioned compounds, and a difunctional urethane (meth)acrylate having a bivalent alkylene group, preferably of three different urethane(meth)acrylates, as well as optionally at least one at least tetrafunctional dendritic urethane(meth)acrylate, preferably at least one hexafunctional dendritic urethane(meth)acrylate.

According to a particularly preferred embodiment, the dental composite material comprises (ii) 10 to 30% by weight of a mixture of at least two different urethane(meth) acrylates, comprising at least one difunctional urethane (meth)acrylate having a bivalent alicyclic that is selected from bis(4',7'-dioxa-3',8'-dioxo-2'-aza-decyl-9'-en)tetrahydrodicyclopentadiene, bis-(4',7'-dioxa-3',8'-dioxo-2'-aza-9'-methyl-decyl-9'-en)tetrahydrodicyclopentadiene and/or mixtures thereof as well as optionally mixtures of the 3,8-/3,9-/4,8-/3,10-/4,10 isomers and/or of the cis isomers and trans isomers of the afore-mentioned compounds, and at least one further difunctional urethane(meth)acrylate, in particular at least one difunctional urethane(meth)acrylate having a bivalent alkylene group, three different urethane (meth)acrylates are preferred, as well as optionally at least one at least tetrafunctional dendritic urethane(meth)acrylate, preferably at least one hexafunctional dendritic urethane (meth)acrylate.

According to a particularly preferred embodiment variant, the dental composite material comprises (ii) a mixture of at least two different urethane(meth)acrylates, preferably of three different urethane(meth)acrylates.

The term(meth)acrylate or urethane(meth)acrylate with (meth) in brackets means that the term may comprise acrylates or urethane acrylates with or without methyl groups.

According to a particularly preferred embodiment variant, the dental composite material comprises ii) 10 to 30% by weight of a mixture of at least two different urethane(meth) acrylates, preferably of at least three different urethane (meth)acrylates, compositing at least a difunctional urethane (meth)acrylate having a bivalent alicyclic group and at least one difunctional urethane(meth)acrylate having a bivalent alkylene group, as well as optionally at least one at least tetrafunctional dendritic urethane(meth)acrylate, preferably at least one hexafunctional dendritic urethane(meth)acrylate.

Particularly preferred difunctional urethane(meth)acrylates having a bivalent alicyclic group comprise or are selected from bis(4',7'-dioxa-3',8'-dioxo-2'-aza-decyl-9'-en) tetrahydrodicyclo-pentadiene, bis(4',7'-dioxa-3',8'-dioxo-2'-aza-9'-methyl-decyl-9'-en)tetrahydrodicyclopentadiene and/or mixtures thereof as well as optionally mixtures of the 3,8-/3,9-/4,8-/3,10-/4,10 isomers and/or of the cis isomers and trans isomers of the afore-mentioned compounds. Particularly preferably, the difunctional urethane acrylate having a bivalent alicyclic group is selected from having a bivalent alicyclic group comprising bis(4',7'-dioxa-3',8'-dioxo-2'-aza-decyl-9'-en)tetrahydrodicyclopentadiene, bis-(4', 7'-dioxa-3',8'-dioxo-2'-aza-9'-methyl-decyl-9'-en)tetrahydrodicyclopentadiene and/or mixtures thereof as well as optionally mixtures of the 3,8-/3,9-/4,8-/3,10-/4,10 isomers and/or of the cis isomers and trans isomers of the aforementioned compounds.

Preferably, the composite material comprises 10 to 20% by weight of a mixture of at least three different urethane (meth)acrylates, selected from 10 to 18% by weight comprising bis-(4',7'-dioxa-3',8'-dioxo-2'-aza-decyl-9'-en)tetrahydrodicyclopentadiene, Bis-(4',7'-dioxa-3',8'-dioxo-2'-aza-9'-methyl-decyl-9'-en)tetrahydrodicyclopentadiene and/or mixtures thereof as well as optionally mixtures of the 3,8-/3,9-/4,8-/3,10-/4,10-isomers and/or of the cis- and trans-isomers of the afore-mentioned compounds, 3 to 8% by weight of a difunctional urethane(meth)acrylate having a bivalent alkylene group, in particular UDMA or HEMA-TMDI, and 0.1 to 2% by weight, preferably 0.2 to 2% by weight, particularly preferably 0.1 to 1% by weight of at least one tetra- to decafunctional dendritic urethane methacrylate, based on the total composition.

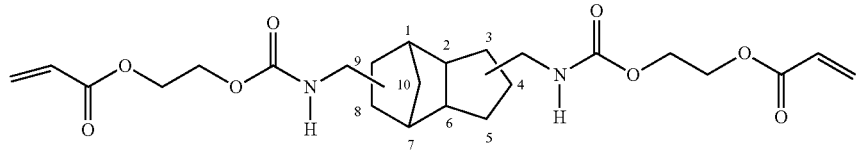

The difunctional urethane(meth)acrylate having a bivalent alicyclic group is preferably selected from linear or branched urethane dimethacrylates being functionalised with a bivalent alkylene group, urethane dimethacrylate-functionalised polyethers having alkylene group(s), such as bis(methacryloxy-2-ethoxycarbonylamino)alkylene, bis(methacryloxy-2-ethoxycarbonylamino)-substituted polyalkylene ethers, preferably 1,6-bis(methacryloxy-2-ethoxycarbonylamino)-2,4,4-trimethylhexane, UDMA with alternative name HEMA-TDMI. A bis(methacryloxy-2-ethoxycarbonylamino)alkylene, wherein alkylene comprises linear or branched C3 to C20, preferably C3 to C6, is preferred, such as, particularly preferably, an alkylene substituted with methyl groups, such as HEMA-TMDI. The bivalent alkylene preferably comprises 2,2,4-trimethylhexamethylene and/or 2,4,4-trimethylhexymethylene.

The at least tetrafunctional dendritic urethane methacrylate comprises tetra- to decafunctional dendritic urethane methacrylates.

It is also preferred for (ii) to comprise 10 to 30% by weight of a mixture of at least two different urethane(meth) acrylates, based on the total composition, preferably 15 to 20% by weight, such as at least one difunctional urethane (meth)acrylate having a bivalent alicyclic group and at least one hexafunctional dendritic urethane(meth)acrylate, and optionally at least one difunctional urethane(meth)acrylate having a bivalent alkylene group.

Preferably, the composite material comprises 5 to 25% by weight, in particular from 15 to 19% by weight bis-(4',7'-dioxa-3',8'-dioxo-2'-aza-decyl-9'-en)tetrahydrodicyclopentadiene, Bis-(4',7'-dioxa-3',8'-dioxo-2'-aza-9'-methyl-decyl-9'-en)tetrahydrodicyclopentadiene and/or mixtures thereof as well as optionally mixtures of the 3,8-/3,9-/4,8-/3,10-/4, 10-isomers and/or of the cis- and trans-isomers of the afore-mentioned compounds, 1 to 15% by weight, in particular 5 to 6% by weight UDMA (1,6-bis(methacryloxy-2-ethoxycarbonylamino)-2,4,4-trimethylhexane), or HEMA-TMDI, and 0.1 to 5% by weight, preferably 0.2 to 2% by weight, particularly preferably 0.1 to 1% by weight of at least one tetra- to decafunctional dendritic urethane methacrylate, based on the total composition.

According to a further preferred embodiment, the dental composite material comprises as component (iii) 0.01 to 5% by weight of at least one di-, tri-, tetra- or multi-functional monomer not being a urethane acrylate and being selected from dimethacrylic esters of polyethers, tri-, tetra- or multi-functional methacrylic esters of polyethers.

Preferably, the content of components (iii) amounts to 0.15 to 5% by weight, particularly preferably 1.0 to 2% by weight, of a dimethacrylic ester of a polyether, such as preferably a dimethacrylate polyethylene glycol, dimethacrylate polypropylene glycol. Dimethacrylate triethylene glycol (TEGDMA), diethylene glycol dimethacrylate (DEGMA) and dimethacrylate tetraethylene glycol (TEDMA) are particularly preferred.

Water as stabilizer was added to the dental composite material to improve the consistency and the flow properties for the process-engineering processability. Stabilizers were added to the composite material to prevent premature polymerization and give the material a certain shelf life. The composite material comprises as preferred stabilizers in component (iv) at least one stabilizer selected from water, at least one benzophenone derivative, preferably alkoxy-substituted benzophenone and/or phenol derivative, such as 2-hydroxy-4-methoxybenzophenone, 2,6-bis(1,1-dimethyl)-4-methylphenol, or a mixture of the three stabilizers. The stabilizers are preferably present in 0.01 to 14% by weight in the total composition, particularly preferably form 0.7 to 10% by weight, in particular from 0.5 to 2% by weight. In addition, it is preferred for the composite material to contain 0.01 to 2% by weight water as stabilizer, preferably 0.1 to 1.0% by weight water.

At least one pigment comprising at least one fluorescence pigment and optionally at least one organic color pigment and/or at least one inorganic color pigment, in particular non-fluorescent color pigments, are added to the composite material for optimal adjustment of the color and natural aesthetic of the polymerized composite material. The at least one fluorescence pigment preferably is an organic fluorescence pigment, in particular a non-polymerisable organic fluorescence pigment, where appropriate comprising aryl carboxylic acid esters, aryl carboxylic acids, coumarin, rhodamine, naphthalene imide or a derivative of the respective substance. Inorganic fluorescence pigments may comprise $CaAl_4O_7:Mn^{2+}$, $(Ba0.98Eu0.02)MgAl_{10}O_{17}$, $BaMgF_4:Eu^{2+}$, $Y(1.995)Ce(0.005)SiO_5$.

The composite may comprise as pigments, in particular color pigments, organic pigments as well as inorganic pigments, in particular comprising diethyl-2,5-dihydroxy terephthalate, N,N'-Bis(3,5-xylyl)perylene-3,4:9,10-bis(dicarbimide), copper phthalocyanine, titanate pigment, in particular chromium antimony titanate (rutile structure), spinel black, in particular pigments being based on iron oxide black ($Fe_3O_4$), wherein iron (Fe) is partially substituted by chromium and copper or nickel and chromium or manganese, zinc iron chromium spinel, brown spinel, ((Zn, Fe)(Fe,Cr)$_2O_4$), cobalt zinc aluminate blue spinel and/or titanium oxide. The pigments comprising fluorescence pigments and color pigments preferably present in 0.01 to 10% by weight in the total composition, particularly preferably from 0.01 to 5% by weight, preferably from 0.01 to 1% by weight.

Selection of pigments has to be specifically adapted to the dental composite composition in order to achieve a homogeneous color in both the polymerisable composite and the polymerized composite. Also the production of large blocks of material requires coordination with regard to the selection and to the concentration of the pigments in order to avoid undesirable discolorations due to the dimensioning of the polymerized blocks of material.

Peroxides, hydroxyl peroxides, optionally azo compounds, or mixtures comprising them are suitable as initiators, in particular thermal initiators or initiator systems. Suitable thermal initiators may be used as radical initiators in the temperature range of 70 to 150° Cm preferably of 90 to 150° C. Preferred thermal initiators comprise at least one initiator selected from: dilauroylperoxide, di-tert.-butylperoxide, tert.-butylperoxy-2-ethylhexanoate, dibenzoylperoxide, dicumylperoxide, dicumylhydroperoxide, 2,2'-azobisisobutyronitrile, benzylbarbituric acid derivative, particularly preferably tert.-butylperoxy-2-ethylhexanoate, dibenzoylperoxide, dicumylperoxide, dicumylhydroperoxide, azobisisobutyronitrile, benzylbarbituric acid derivative.

According to a further particularly preferred embodiment, the dental composite material comprises component (i) forming the filler component, wherein the filler component comprises (i.1) 85 to 95% by weight of at least one dental glass, in particular from 90 to 94.5% by weight, preferably from 92 to 94.5% by weight, and optionally (i.2) from 5 to 15% by weight amorphous metal oxide, in particular 5 to 10% by weight, preferably 5.5 to 8% by weight, in the filler component, wherein (i.1) and (i.2) amounts to 100% by weight of the filler component.

According to a further particularly preferred embodiment, the dental composite material comprises components (ii) and (iii) forming the monomer component, wherein the monomer component comprises (ii.1) 55 to 75% by weight of at least one bis(4',7'-dioxa-3',8'-dioxo-2'-aza-decyl-9'-en)tetrahydrodicyclopentadiene, bis(4',7'-dioxa-3',8'-dioxo-2'-aza-9'-methyl-decyl-9'-en)tetrahydrodicyclopentadiene and/or mixtures thereof as well as optionally mixtures of the 3,8-/3,9-/4,8-/3,10-/4,10-isomers and/or of the cis isomers and trans isomers of the afore-mentioned compounds, and (ii.2) 21 to 38% by weight of at least one difunctional urethane(meth)acrylate having a bivalent alkylene group, as well as optionally (ii.3) 0.1 to 14% by weight, in particular 0.2 to 9% by weight of at least one tetra- to decafunctional dendritic urethane methacrylate, in particular a dendritic six-fold urethane methacrylate, and (iii) 1 to 10% by weight of at least one di-, tri-, tetra- or multi-functional monomer not being a urethane(meth)acrylate, wherein the monomers (ii.1), (ii.2), (ii.3) and (iii) amounts to 100% by weight in the monomer component.

Another subject matter of the invention is a polymerized dental composite material obtainable by polymerization of the composite material according to the invention, in particular by polymerization of the composite material at a pressure of 500 to 300 MPa (=[N/mm$^2$]), in particular at 50 to 300 MPa, preferably at 100 to 300 MPa, particularly preferably at 120 to 200 MPa, preferably at 120 to 170 MPa, and/or elevated temperature, preferably at 90 to 150° C. Polymerization is preferably carried out in a casting mould, preferably having a geometric shape. The polymerization under elevated pressure minimises or avoids air bubble formation in the polymerized composite material.

The shrinkage of the polymerisable composite material preferably amounts to less than or equal to 2.0%, in particular less than 1.5%, particularly preferably less than or equal to 1.4% ((Bonded-Disc method—Dental Materials, Watts et al, (2004) 20, 88-95; 23° C., Translux Energy, 60 s exposure).

The polymerized composite material preferably has no blowholes or cracks of a size of greater than or equal to 200 nm, in particular a block of material has no blowholes or cracks. The polymerized composite material has a density of greater than or equal to 2.0 g/cm$^3$, in particular a density of greater than or equal to 2.1 g/cm$^3$.

Surprisingly, the polymerized dental composite material, in particular being obtainable by thermal polymerization of the composite material, has a synergistic combination of a high flexural strength and of an elastic modulus in the range of the hard tooth tissue. The flexural strength and the elastic modulus may be measured by keeping thermally polymerized test specimens for 7 days under dry conditions at ambient room temperature (23±2° C.) or by storing test specimens in 37° C. deionized water for 7 days, followed by 5000 thermal cycles (5° c. to 55° c., retention time 30 s) by means of a thermocyclic device (HA-K178, Tokyo Giken Inc., Tokyo, Japan) and subsequently measuring flexural strength and e-modulus. Surprisingly the polymerized dental composite material, in particular being obtainable by thermal polymerization of the composite material, has a flexural strength of greater than or equal to 210 MPa, preferably greater than or equal to 220 MPa and an e-modulus of greater than or equal to 16 to 20 GPa, preferably of greater than or equal to 17 GPa to 20 GPa, further preferably of 18 to 20 GPa (7 days, 23±2° C., dry) according to EN ISO 6872:2008 and a flexural strength of greater than or equal to 160 MPa to 260 MPa (7 days of storage in H$_2$O deionized at 37° C., followed by greater than or equal to 1000 cycles, in particular 5000 cycles (5° C. to 55° C., retention time greater than or equal to 30 seconds, optionally to 60 seconds)) and an elastic modulus greater than or equal to 14 to 21 GPa (7 days of storage in H$_2$O deionized at 37° C., followed by greater than or equal to 1000 cycles, in particular 5000 cycles (5° C. to 55° C., retention time greater than or equal to 30 seconds)), according to EN ISO 6872: 2008. The flexural strength and the elastic modulus were prepared and measured (dry as well as after 7 days of storage in water with thermocycling) analogous to Dent. Materials J 2014; 33(4/5), 705 to 710, i.e. according to EN ISO 6872:2008 or with additional water storage.

The ISO 6872 standard was developed for testing ceramic materials being available as CAD/CAM blocks. Since the composite materials are also produced and machined in the same dimensioning, a comparable analogous test with water storage should be carried out. The production of test specimens according to the composite standard (ISO4049) cannot be carried out from one block due to the dimensions of the test specimens. While the flexural strength of a dental composite is not limited to high values, (>100 MPa), a balanced/optimal elasticity is advantageous for the application. The elastic modulus should ideally correspond to that of the dentin of the hard tooth tissue so that failure in the intended application is avoided as far as possible. Materials that are too brittle (having a high e-modulus) tend to chipping or fracture. Materials that are too elastic (low e-modulus) deform under chewing load and the cementation detaches (debonding).

The material properties (flexural strength and e-modulus) of human hard tooth tissue are known from literature (Dwayne D. Arola et al. Biomaterials 27(2006) 2131-2140) as a function of orientation (anisotropic material properties due to crystal orientation). There, the elastic modulus of human hard tooth structure is between 15 to 19 GPa, depending on the orientation. The aim was therefore to provide a composite having an e-modulus (elastic modulus) being in the range of human hard tooth tissue, thus preferably in the range of 15 to 20 GPa, to mimic toothlike properties.

Thus, another subject matter of the invention is a polymerized dental composite material, in particular a thermally polymerized composite material, which has preferably been polymerized for 10 minutes to 10 hours at 80 to 150° C., a composite material being polymerized at 90 to 150° C. is preferred, as well as a composite material being obtainable by thermal polymerization, having a flexural strength of greater than or equal to 200 MPa to 260 MPa (7 days, 23±2° C., dry) and an elastic modulus greater than or equal to 15 to 20 GPa (7 days, 23±2° C., dry), according to EN ISO 6872:2008, in particular having a flexural strength of greater than or equal to 210 MPa, preferably greater than or equal to 220 MPa and an e-modulus of greater than or equal to 16 to 20 GPa, preferably of greater than or equal to 17 to 20 GPa, further preferably of 18 to 20 GPa. Another subject matter of the invention is a polymerized composite material, in particular a thermally polymerized composite material having a flexural strength of greater than or equal to 160 MPa to 260 MPa (7 days of storage in $H_2O$ deionized at 27° C., followed by greater than or equal to 1000 cycles (5° C. to 55° C., retention time greater than or equal to 30 seconds) and an elastic modulus of greater than or equal to 14 to 21 GPa (7 days of storage in $H_2O$ deionized at 27° C., followed by greater than or equal to 1000 cycles (5° C. to 55° C., retention time greater than or equal to 30 seconds) according to EN ISO 6872:2008, in particular having a flexural strength of greater than or equal to 170 MPa, preferably greater than or equal to 210 MPa and an e-modulus of greater than or equal to 15 to 21 GPa, preferably of greater than or equal to 16 GPa to 20 GPa, further preferably of 18 to 20 GPa.

The afore-mentioned publication also compares in Table 3 further measurement results of the three-point bending flexural test for CAD/CAM blocks of different dental materials. The dental materials measured therein have flexural strengths after dry storage of 170 MPa and an e-modulus of 9.6 or 14.5 GPa, as well as a flexural strength of 117.6 MPa or 120.1 and an e-modulus of 7.2 or 12.2 GPa after thermocycling. Even dental materials having a flexural strength of 242 or 204 MPa and an e-modulus of 10.0 or 14.7 GPa after dry storage only have flexural strengths of 194.3 or 165.1 MPa at an e-modulus of 8.7 GPa or 13.2 GPa. It is therefore clear that setting an e-modulus analogous to that of the hard tooth tissue in the range of 15 to 20 GPa at both dry storage and also a storage at 37° C. plus thermocycling had not been possible so far.

TABLE 1

Flexural strength in MPa and e-modulus in GPa of Table 3 in Dent. Mater. J. 2014; 33(5) 705-710

| | Condition | Block HC | Cera-smart | Gradia Block | Lava Ulti-mate | Vita Enamic | Vita-blocs Mark II |
|---|---|---|---|---|---|---|---|
| flexural strength [MPa] | dry | 170.5 | 242.0 | 204.0 | 170.5 | 140.7 | 126.6 |
| | water | 121.5 | 197.3 | 188.4 | 141.9 | 133.0 | 121.1 |
| | water/TC | 117.6 | 194.3 | 165.1 | 120.1 | 134.6 | 129.0 |
| e-modulus [GPa] | dry | 9.6 | 10.0 | 14.7 | 14.5 | 28.5 | 51.5 |
| | water | 7.8 | 9.0 | 13.5 | 12.8 | 28.3 | 52.8 |
| | water/TC | 7.2 | 8.7 | 13.2 | 12.2 | 28.6 | 54.9 |

According to a particularly preferred embodiment, a subject matter of the invention is polymerized dental composite material comprising 70 to 85% by weight of at least one inorganic filler component comprising at least one dental glass of an average particle size $d_{50}$ in the range of 0.8 to 5.5 µm and preferably $d_{99}$ less than or equal to 7.5 µm, as well as optionally at least one amorphous silanised metal oxide, in particular precipitated silicon dioxide and/or pyrogenic silica of a primary particle size of 2 to 45 nm, 10 to 30% by weight of at least one polymer being based on at least one monomer, preferably being based on a mixture of the following monomers, comprising at least one bis-urethane derivative of tetrahydrodicyclopentadiene, in particular a difunctional urethane(meth)acrylate of tetrahydrodicyclopentadiene and at least one diurethane(meth)acrylate having a bivalent alkylene group, at least one tetra- to decafunctional dendritic urethane methacrylate, and at least one di-, tri-, tetra- or multi-functional methacrylic ester of polyethers, preferably dimethacrylate triethylene glycol, and 0.01 to 10% by weight of at least one pigment, in particular of at least one fluorescence pigment and of at least one organic colour pigment and/or of at least one inorganic color pigment, wherein the color pigments preferably do bot fluoresce, wherein the total composition of the composite material amounts to 100% by weight.

The polymerized dental composite material may preferably be present in the form of a block of material, in particular as three-dimensional block of material in the form of a geometric moulded body, in particular in the form of a milling blank with an adapter for fastening in an automated device to remove material, particularly preferably in the form of a cylinder, of a cuboid, preferably in the form of a cube. In addition, it is preferred for the edges and/or vertices of the moulded body to be rounded. The dimensions of the cylinder preferably are: height greater than or equal to 10 mm to less than or equal to 15 mm with a radius of greater than or equal to 3 to less than or equal to 7 mm, alternatively with a height of greater than or equal to 10 mm to less than or equal to 20 mm and a radius of greater than or equal to 5 to less than or equal to 7 mm. The dimensions of the cuboid for a, b, and c preferably amounts to greater than or equal to 4 mm, in particular greater than or equal to 10 mm and a less than or equal to 20 mm, in particular less than or equal to 18 mm, b less than or equal to 14 mm and c less than or equal to 20 mm, in particular less than or equal to 18 mm. Preferably, a three-dimensional block of material as at least an edge length of at least 10 mm each, preferably of 14 mm. Blocks of material being us as milling blanks preferably have the shape of cuboids, wherein the cuboids preferably have a volume of 12 mm×14 mm×17 or 18 mm, alternatively of 14×14 mm, or 15×15 mm as well as a height of 17 to 18 mm. One to all edges and vertices may be straight or rounded.

Furthermore, a subject matter of the invention is the use of a dental composite material for the production of dental prosthetic restorations, in particular for the production of indirect dentures, in a material-removing process, in particular in a process in which the polymerized composite material is removed by means of milling, cutting, polishing, breaking, chipping and/or drilling, particularly preferably in a process in which the composite material is removed by means of laser energy. A particularly preferred use for the material is the use in a method for the production of dental prosthetic restorations in a material-removing process, in which the material is removed by means of laser energy. The particle size as well as preferably the particle size distribution was specially adapted to a method in which the polymerized composite material is removed by means of laser energy and the prosthetic restorations may be produced. or for the production of direct adhesive dental restorations. A particular advantage of the dental material according to the invention is that it allows the possibility of a significant process simplification in the production of indirect dentures by the dentist or dental technician carrying out at least one intraoral scan in the patient's mouth and may subsequently use the digital dental information obtained in this way to directly fabricate a prosthetic dental restoration, such as a crown or an inlay, taking into account other device parameters, etc. The dental prosthetic restoration produced may then be inserted at the patient, fixed and, if necessary, slightly reprocessed. For example, an intraoral scan is taken before grinding a tooth to produce a tooth stump for a crown and another intraoral scan of the tooth stump.

Furthermore, the polymerized composite material may be used for the production of dental prosthetic restorations comprising crowns, inlay, onlays, superstructures, artificial teeth, dental bridges, dental bars, spacers, abutments or veneers. The polymerized composite material may additionally be used as composite material for the production of direct adhesive dental restorations.

The following are also preferably considered to be urethane(meth)acrylates according to the invention: (ii) at least one urethane(meth)acrylate, in particular a urethane dimethacrylate, preferably a bis(methacryloxy-2-ethoxycabonylamino)alkylene, diurethane acrylate oligomers, alkyl-functional urethane dimethacrylate oligomers, aromatic-functionalised urethane dimethacrylate oligomers, aliphatic unsaturated urethane acrylates, bis(methacryloxy-2-ethoxycarbonylamino)-substituted polyethers, aromatic urethane diacrylate oligomers, aliphatic urethane diacrylate oligomers, aliphatic urethan diacrylates, hexafunctional aliphatic urethane resins, aliphatic urethane triacrylates, aliphatic urethane acrylate oligomers, unsaturated aliphatic urethane acrylates. Difunctional and multi-function urethane(meth)acrylates are preferred, such as, in particular, urethane di(meth)acrylate, the at least one (iii) urethane dimethacrylate is particularly preferably selected from linear or branched alkyl-functionalised urethane dimethacrylates, urethane dimethacrylate-functionalised polyethers, in particular bis(methacryloxy-2-ethoxycarbonylamino)alkylene, bis(methacryloxy-2-ethoxycarbonylamino)-substituted polyethers, preferably 1,6-bis(methacryloxy-2-ethoxycarbonylamino)-2,4,4-trimethylhexane. Suitable urethane(meth)acrylates are available under the following brand names: Ebecryl 230 (aliphatic urethane diacrylate), Actilane 9290, Craynor 9200 (Diurethane acrylate oligomer), Ebecryl 210 (aromatic urethane diacrylate oligomers), Ebecryl 270 (aliphatic urethane diacrylate oligomers), Actilane 165, Actilane 250, Genomer 1122 (monofunctional urethane acrylate), Photomer 6210 (cas no. 52404-33-8, aliphatic urethane diacrylate), Photomer 6623 (hexa-functional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate). The urethane(meth)acrylates may preferably be selected from the afore-mentioned urethane(meth)acrylates or from a mixture of at least two different, preferably at least three different, afore-mentioned urethane(meth)acrylates.

The at least one di-, tri-, tetra- or multi-functional monomer not being urethane(meth)acrylate is preferably selected from at least one of the following monomers, in particular a mixture of monomers comprising 1,4-butandiol dimethacrylate (1,4-BDMA) or pentaerythritol tetraacrylate, bis-GMA monomer (bisphenol-A-glycidyl methacrylate), triethylene glycol dimethacrylate (TEGDMA) and diethylene glycol dimethacrylate (DEGMA), tetraethylene glycol di(meth)acrylate, decanediol di(meth)acrylate, dodecandiol di(meth)acrylate, hexyldexandiol di(meth)acrylate, trimethylolpropane tri(meth)acrylate, pentaerythritol tetra(meth)acrylate as well as butanediol di(meth)acrylate, ethylene glycol di(meth)acrylate, polyethylene glycol di(meth)acrylate, ethoxylated/propoxylated bisphenol-A-di(meth)acrylate, of a mixture comprising at least one of these (meth)acrylates and/or copolymers comprising one or at least two of the aforementioned monomers.

Typical difunctional monomers, also referred to as crosslinker and/or multi-crosslinker, include tri- or tetraethylene glycol di(meth)acrylate, BDMA, 1,4-butandiol dimethacrylate (1,4-BDMA), bis-GMA monomer (bisphenol-A-glycidylmethacrylate, an addition product of methacrylic acid and bisphenol-A diglycidylether), diethylene glycol di(meth)acrylate, bisphenol-A di(meth)acrylate, decanediol di(meth)acrylate, dodecandiol di(meth)acrylate, hexyldexandiol di(meth)acrylate as well as butanediol di(meth)acrylate, ethylene glycol di(meth)acrylate, polyethylene glycol di(meth)acrylate, ethoxylated/propoxylated bisphenol-A-di(meth)acrylate. The following difunctional monomers may also be added as diluting agent (low viscosity acrylates). Tri- and tetrafunctional monomers and/or multi-crosslinkers comprise trimethylolpropane tri(meth)acrylate, tris(2-hydroxyethyl)-isocyanurate triacrylate, pentaerythritol tetraacrylate.

At least one of the following monomers may be present in the composite material in addition to the di-, tri- or multi-functional monomer or monomers, comprising at least one monomer, in particular a mixture of monomers of methylmethacrylate, ethylmethacrylate, propylmethacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, benzyl-, furfuryl- or phenyl (meth)acrylate, a mixture containing at least one of these (meth)acrylates and/or copolymers comprising one or at least two of the aforementioned monomers.

Furthermore, a subject matter of the invention is a composite material comprising, preferably additionally, at least one or more substance(s) from the groups consisting of fillers, pigments, stabilisers, regulators, antimicrobial additives, UV-absorbing agents, thixotroping agents, catalysts and crosslinkers. Rather small amounts of said additives—as also of pigments, stabilisers and regulators—are used, e.g. a total of 0.01 to 3.0, in particular 0.01 to 1.0% by weight, based on the total mass of the material. Suitable stabilizers include e.g. hydroquinone monomethylether or 2,6-di-tert.-butyl-4-methylphenol (BHT).

The following initiators and/or initiator systems for auto- or cold-polymerization comprise a) at least one initiator, in particular at least one peroxide and/or azo compound, in particular LPO: dilauroylperoxide, BPO: dibenzoylperoxide, t-BPEH: tert.-butyl-peroxy-2-ethylhexanoate, AIBN: 2,2'-azobis-(isbutyronitrile), DTBP: di-tert-butylperoxide, and, optionally, b) at least one activator, in particular at least one aromatic amine, such as N,N-dimethyl-p-toluidine, N,N dihydroxyethyl-p-toluidine and/or p-dimethylaminobenzoic acid diethylester, or c) at least one initiator system selected from redox systems, in particular a combination selected from dibenzoylperoxide, dilauroylperoxide, and camphorquinone with amines selected from N,N dimethyl-p-toluidine, N,N-dihydroxyethyl-p-toluidine, and p-dimethyl-amino-benzoic acid diethylester. The initiator may alternatively be a redox system comprising a peroxide, and a reduction agent selected from ascorbic acid, ascorbic acid derivative, barbituric acid or a barbituric acid derivative, sulfinic acid, sulfinic acid derivative, particularly preferred is a redox system comprising (i) barbituric acid or thiobarbituric acid or a barbituric acid derivative or thiobarbituric acid derivative, and (ii) at least one copper salt or copper complex, and (iii) at least one compound having an ionic halogen atom, particularly preferred is a redox system comprising 1-benzyl-5-phenylbarbituric acid, copper acetylacetonate, and benzyldibutylammonium chloride. Particularly preferably, the polymerisation in the two-component prosthetic base material is started by a barbituric acid derivative.

In general, Initiators for the polymerization reaction of cold- or auto-polymerizing starting mixtures are considered to be those with which radical polymerization reactions may be started. Preferred initiators are peroxides as well as azo compounds, such as, for example, the following: LPO: dilauroylperoxide, BPO: dibenzoylperoxide, t-BPEH: tert.-butylperoxi-2-ethylhexanoate, AIBN: 2,2'-azobis-(isobutyronitrile), DTBP: di-tert.-butylperoxide.

In order to accelerate the initiation of radical polymerization by peroxides, suitable activators, e.g. aromatic amines, may be added. Examples of suitable amines are N,N-dimethyl-p-toluidine, N,N-dihydroxyethyl-p-toluidine and p-dibenzylaminobenzoic acid diethylester. In this context, the amines regularly function as co-initiators and are usually present in an amount of up to 0.5% by weight.

The below execution examples shall clarify the invention without limiting it to these examples.
Execution Examples:
Three-Point Bending Flexural Test The flexural properties were determined using a three-point bending flexural test according to ISO 6872:2008 (ISO 6872:2008. Dentistry—Ceramic materials, 3rd ed, International Organization for Standardization, Geneva, 2008). The rod-shaped specimens, 4.0 mm wide, 14.0 mm long and 1.2 mm thick, were produced with a low-speed diamond saw (Isomet, Buehler, Lake Bluff, Ill., USA). All specimens were wet ground and polished with a #600 and #1000 diamond wheel (Maruto, Tokyo, Japan) and #1000 diamond blades (Maruto) mounted on a metallographic lapping machine (Dia-Lap, ML-150P, Maruto) to achieve the required dimensions of 4.0±0.2×14.0±0.2×1.2±0.2 mm. In order to minimize edge breaks in the rod-shaped specimens during the bending test, an edge chamfer, 0.15 mm wide, was incorporated using the lapping machine with a #1000 diamond blade. After polishing, all specimens were stored in a silica gel desiccator for 7 days prior to the bending flexural test. Three groups of ten specimens each were randomly produced from each CAD/CAM block. Specimens of the first group were stored under dry conditions at ambient room temperature (23±2° C.) for 7 days. The second group was stored in 37° C. deionized water for 7 days, while the third group was stored in 37° C. deionized water for 7 days followed by 5000 thermal cycles (Thermal cycles=TZ, 5° C. to 55° C., retention time 30 s) using a thermocyclic device (HA-K178, Tokyo Giken Inc., Tokyo, Japan). The width and thickness of each specimen were measured using a digital micrometer (MDC-25M, Mitsutoyo Co., Tokyo, Japan; minimum value: 0.001 mm). A three-point bending flexural test with a support span of 12.0 mm and a traverse speed of 1.0 mm/min was performed at ambient room temperature (23±2° C.) by means of a universal testing machine (AG-X, Shimadzu Corp., Kyoto, Japan). The flexural strength and the flexural modulus were calculated by use of software (TRAPEZIUM X, Shimadzu Corp., Kyoto, Japan). The flexural modulus (E) was calculated according to the following formula:

$$E = FL^3/4bh^3d$$

wherein F represents the load at an appropriate point in the linear part of the spring characteristics, L the support span (12.00 mm), b the width of the specimen, h the thickness of the specimen and d the bending at a load F. The flexural strength (δ) was calculated with the following formula:

$$\delta = 3F_1 L/2bh^2$$

wherein $F_1$ represents the maximal load during the bending flexural test.

The hardness test was carried out using a Zwick universal device: The measured values of the specimens according to the invention are in the range of 800 to 850.

In the following, comparative examples of light-curing products Venus Diamond (VD) and Venus Pearl (VP) have been measured according to ISO 4049 and ISO 6872 (The exposure was carried out point by point according to the method described in EN ISO 4049:2009 7.11 using a Translux 2Wave (1200 mW/cm$^2$) by means of an exposure time of respectively 20 seconds per exposure point) and compared with Example 1 according to the invention.

TABLE 2

Comparison Ex. 1 with Venus products

| | | Comparative examples | |
|---|---|---|---|
| | Example 1 | Venus Diamond (VD) | Venus Pearl (VP) |
| Flexural strength [MPa] according to EN ISO 6872 (24 h/water) | 209 MPa | 182 MPa | 195 MPa |
| Elastic modulus [GPa] according to EN ISO 6872 (24 h/water) | 15.7 GPa | 15.6 GPa | 15.8 GPa |
| Flexural strength [MPa] according to EN ISO 4049 (24 h/water) | | 174 MPa | 149 MPa |
| Elastic modulus [GPa] according to EN ISO 4049 (24 h/water) | | 12.0 GPa | 11.4 GPa |

TABLE 3

Examples 1 to 3

| dental | | Example 1 1.3 μm | | Example 2 1.8 μm | | Example 3 1.5 μm |
|---|---|---|---|---|---|---|
| glass | average diameter d$_{50}$ | % by weight | g | % by weight | g | % by weight |
| dental glass | bariumaluminumboro-fluorsilicate glass (silanised) | 69.11 | 69 | 76.01 | 76 | 69.3 |
| metal oxide | amorphous SiO$_2$ | 5.51 | 5.5 | 4.50 | 4.5 | 7 |
| urethane (meth)-acrylates | bis(4',7'-dioxa-3',8'-dioxo-2'-aza-decyl-9'-en)tetrahydro-dicyclopentadiene | 14.62 | 14.6 | 12.00 | 12 | 14.8 |
| | urethane methacrylate dendrimer, hexafunctional | 0.70 | 0.7 | 0.60 | 0.6 | 0.6 |
| | 7,7,9-trimethyl-4,13-dioxo-3,14-dioxa-5,12-diaza-hexadecane-1,16-diylbismethacrylate | 5.31 | 5.3 | 4.50 | 4.5 | 5.3 |
| di- to multi-functional monomers | 1,2-bis(2-(meth-acryloyloxy)-ethoxy)ethane | 1.20 | 1.2 | 1.00 | 1 | 1.3 |
| | 1,12-dodecanediol dimethacrylate | 1.40 | 1.4 | | | |
| initiator system | tert--butylperoxy-2-ethylhexanoate | 0.50 | 0.5 | 0.50 | 0.5 | 0.5 |
| stabilizer | 2,6-Bis(1,1-dimethyl-ethyl)-4-methyl-phenol | 0.04 | 0.04 | 0.04 | 0.04 | 0.04 |
| | 2-hydroxy-4-methoxy-benzophenone | 0.30 | 0.3 | 0.25 | 0.25 | 0.3 |
| | water | 0.60 | 0.6 | 0.00 | | 0.45 |
| pigments and others | diethyl-2,5-dihydroxy-terephthalate, color pigments | 0.70 | 0.7 | 0.60 | 0.6 | 0.45 |

Polymerization of the dental composites according to the invention was usually performed for ca. 3 h at 95° C.

TABLE 4

Flexural strengths (according to EN ISO 6872)

| | 7 days (RT) dry | after 24 h/water | 7 days/water | after TZ/water |
|---|---|---|---|---|
| Example 1 | | 209 MPa | | 179 MPa |
| Example 2 | | 221 MPa | 173 MPa | 226 MPa |
| Example 3 | 236* MPa 245** MPa | | 227 MPa | 226 MPa |
| Example 4 | 205 MPa 220 MPa | | 170 MPa | 165 MPa |
| Example 5[1)] | 232 MPa | | | |
| Example 6[2)] | 205 MPa | | | |

*after polymerization,
**after 7 days,
[1)] particle size distribution three dental glass fractions according to b) 2 to 3:1:6 to 7,
[2)] particle size distribution according to a) with d$_{50}$ of 1.5 μm

TABLE 5

E-modulus (elastic modulus)

| | 7 days (RT) dry | after 24 h/water | 7 days/water | after TZ/water |
|---|---|---|---|---|
| Example 1 | | 15.7 GPa | | 14.5 GPa |
| Example 2 | | 16.8 GPa | | 15.5 GPa |
| Example 3 | 16* GPa 17.7** GPa | | 16.8 GPa | 19.6 GPa |
| Example 4 | 16.9* GPa 18.4 GPa** | | 16.2 GPa | 16.8 GPa |
| Example 5[1)] | 18.5 GPa | | | |
| Example 6[2)] | 16.8 GPa | | | |

*after polymerization,
**after 7 days,
[1)] particle size distribution three dental glass fractions according to b) 2 to 3:1:6 to 7,
[2)] particle size distribution according to a) with d$_{50}$ of 1.5 μm

The invention claimed is:

1. A polymerisable dental composite material, comprising
(i) 70 to 85% by weight of an inorganic filler component comprising a mixture of dental glasses of different fractions having an average particle size, with i) d$_{50}$ of 2 to 8 μm, ii) d$_{50}$ of 1.0 to 2.0 μm, and iii) d$_{50}$ of 0.5 μm to 1.2 μm, wherein the fractions of i) to ii) to iii) are present in a ratio of 1 to 4:1:4 to 8, as well as optionally at least one amorphous metal oxide,
(ii) 10 to 30% by weight of a mixture of at least two different
urethane(meth)acrylates, wherein the mixture comprises at least one difunctional urethane(meth)acrylate having a bivalent alicyclic group comprising bis-(4',7'-dioxa-3',8'-dioxo-2'-aza-decyl-9'-en)tetrahydrodicyclopentadiene, bis-(4',7'-dioxa-3', 8'-dioxo-2'-aza-9'-methyl-decyl-9'-en)tetrahydrodicyclopentadiene and/or mixtures thereof, as well as optionally mixtures of the 3,8-/3,9-/4,8-/3,10-/4,10 isomers and/or of the cis isomers and trans isomers of the afore-mentioned compounds,
(iii) 0.01 to 5% by weight of at least one di-, tri-, tetra- or multi-functional monomer not being a urethane(meth)acrylate,
(iv) 0.01 to 10% by weight of at least one initiator, of an initiator system, as well as
optionally of at least one stabilizer and optionally of at least one pigment, wherein the total composition of the composite material amounts to 100% by weight.

2. The dental composite material according to claim 1, wherein the amorphous metal oxide comprises at least one non-agglomerated amorphous metal oxide having a primary particle size of 2 to 45 nm, and the amorphous metal oxide optionally comprises precipitated silicon dioxide, pyrogenic silica, zirconium oxide or mixed oxides.

3. The dental composite material according to claim 1, wherein the composite material comprises as (i) inorganic filler component
(i.1) 70 to 84% by weight of at least one dental glass, and optionally
(i.2) 1 to 15% by weight amorphous metal oxide, based on the total composition.

4. The dental composite material according to claim 1, wherein (ii) comprises a mixture of at least two different urethane(meth)acrylates, wherein the mixture comprises at least one difunctional urethane(meth)acrylate having a bivalent alicyclic group and a difunctional urethane(meth)acrylate having a bivalent alkylene group, and optionally at least one at least tetrafunctional dendritic urethane(meth)acrylate.

5. The dental composite material according to claim 1, wherein (iii) is selected from di-methacrylic esters of polyethers, tri-, tetra- or multi-functional methacrylic esters of polyethers.

6. The dental composite material according to claim 1, wherein the at least one stabilizer comprises water, at least one benzophenone derivative and/or at least one phenol derivative.

7. The dental composite material according to claim 1, wherein the at least one pigment comprises fluorescence pigments, organic color pigments, as well as inorganic color pigments.

8. A polymerized dental composite material obtained by polymerization of the composite material according to claim 1.

9. The polymerized dental composite material according to claim 8 having a flexural strength of greater than or equal to 200 MPa to 260 MPa after 7 days, at 23±2° C., and dry storage and an elastic modulus greater than or equal to 15 to 20 GPa after 7 days, at 23±2° C., and dry storage according to EN ISO 6872:2008.

10. The polymerized dental composite material according to claim 8 having a flexural strength of greater than or equal to 160 MPa to 260 MPa after 7 days of storage in $H_2O$ deionized at 37° C., followed by greater than or equal to 1000 cycles, at 5° C. to 55° C., with a retention time greater than or equal to 30 seconds and an elastic modulus greater than or equal to 14 to 21 GPa after 7 days of storage in $H_2O$ deionized at 37° C., followed by greater than or equal to 1000 cycles at 5° C. to 55° C., with a retention time greater than or equal to 30 seconds according to EN ISO 6872:2008.

11. A polymerized dental composite material according to claim 9, comprising
70 to 85% by weight of at least one inorganic filler compound comprising a mixture of dental glasses of different fractions having an average particle size, with i) $d_{50}$ of 2 to 8 µm, ii) $d_{50}$ of 1.0 to 2.0 µm, and iii) $d_{50}$ of 0.5 µm to 1.2 µm, wherein the fractions of i) to ii) to iii) are present in the ratio of 1 to 4:1:4 to 8, as well as optionally at least one amorphous silanised metal oxide of a primary particle size of 2 to 45 nm,
10 to 30% by weight of at least one polymer being based on at least one monomer comprising at least one bis-urethane derivative of tetrahydrodicyclopentadiene, at least one di-urethane(meth)acrylate having a bivalent alkylene group, at least one tetra- to decafunctional dendritic urethane methacrylate, and at least one di-, tri-, tetra- or multi-functional methacrylic ester of polyethers, and
0.01 to 10% by weight of at least one pigment, wherein the total composition of the composite material amounts to 100% by weight.

12. The polymerized dental composite material according to claim 8, wherein the polymerized dental composite material is present in the form of a block of material.

13. Method of using a dental composite material according to claim 1 for the production of dental prosthetic restorations in a material-removing process, or for the production of direct adhesive dental restorations, as hoof repair material, as bone cement, as bone cement for cementing artificial joint prostheses, orthodontic apparatuses and instruments.

14. Method according to claim 13 for the production of dental prosthetic restorations comprising crowns, inlay, onlays, superstructures, artificial teeth, dental bridges, dental bars, spacers, abutments or veneers.

15. The polymerized dental composite according to claim 11, obtained by polymerization at a pressure of 50 to 300 MPa and/or elevated temperature at 90 to 150° C. for 10 minutes to 10 hours.

16. The polymerized dental composite material according to claim 11, wherein the polymerized dental composite material is present in the form of a block of material.

17. Method of using a dental composite material according to claim 8 for the production of dental prosthetic restorations in a material-removing process, or for the production of direct adhesive dental restorations, as hoof repair material, as bone cement, as bone cement for cementing artificial joint prostheses, orthodontic apparatuses and instruments.

18. Method of using a dental composite material according to claim 11 for the production of dental prosthetic restorations in a material-removing process, or for the production of direct adhesive dental restorations, as hoof repair material, as bone cement, as bone cement for cementing artificial joint prostheses, orthodontic apparatuses and instruments.

* * * * *